(12) United States Patent
Moe et al.

(10) Patent No.: US 6,283,994 B1
(45) Date of Patent: Sep. 4, 2001

(54) HEART VALVE LEAFLET

(75) Inventors: Riyad E. Moe; Edward J. Sarnowski, both of Austin; Xiao-Yan Gong, Round Rock, all of TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/292,914

(22) Filed: Apr. 16, 1999

(51) Int. Cl.⁷ ....................................................... A61F 2/24
(52) U.S. Cl. ............................................................ 623/2.12
(58) Field of Search ..................................... 623/2.1, 2.12, 623/2.13, 2.14, 2.15, 2.16, 2.17, 2.18, 2.19

(56) References Cited

U.S. PATENT DOCUMENTS

| | | | |
|---|---|---|---|
| 4,222,126 | * 9/1980 | Boretos et al. | 623/2.19 |
| 4,364,127 | 12/1982 | Pierce et al. | 3/1.5 |
| 4,372,743 | * 2/1983 | Lane | 623/2.12 |
| 4,759,759 | * 7/1988 | Walker et al. | 623/2.16 |
| 4,778,461 | * 10/1988 | Pietsch et al. | 623/2.13 |
| 5,376,113 | 12/1994 | Jansen et al. | 623/2 |
| 5,500,016 | 3/1996 | Fisher | 623/2 |

FOREIGN PATENT DOCUMENTS

| | | |
|---|---|---|
| 196 24 948 A1 | 2/1998 | (DE) . |
| 196 25 202 A1 | 2/1998 | (DE) . |
| 2 788 217 A1 | 7/2000 | (FR) . |
| WO 98/32400 | 7/1998 | (WO) . |

OTHER PUBLICATIONS

Knierbein, B., et al., Cad–Design, Stress Analysis and In Vitro Evaluation of Three Leaflet Blood–Pump Valves, J. Biomed. Eng. 1992, vol. 14, Jul., pp. 275–286.

* cited by examiner

Primary Examiner—David J. Isabella
(74) Attorney, Agent, or Firm—Phillip S. Lyren; Timothy L. Scott; Blossom E. Loo

(57) ABSTRACT

A heart valve is disclosed which includes a valve body and a plurality of flexible leaflets coupled to the valve body. The plurality of leaflets has an open position and a closed position. Each of the plurality of leaflets comprises a belly when the plurality of leaflets are in their respective closed positions. The belly of one or more of the plurality of leaflets has a continuous curvature except for a non-continuous portion.

23 Claims, 19 Drawing Sheets

HEART VALVE LEAFLET

FIELD OF THE INVENTION

The present invention is related to valves and in particular to heart valve prostheses having a plurality of flexible leaflets.

BACKGROUND OF THE INVENTION

Ever since 1950, when blood oxygenators made open heart surgery feasible, it has been possible to treat some forms of heart disease by replacing one of the patient's heart valves with a prosthetic valve. Early heart valve prostheses included ball-and-cage valves and disc-and-cage valves in which a ball or a disc was housed in a cage. One side of the cage provided an orifice through which blood flowed either into or out of the heart, depending on the valve being replaced. When blood flowed in a forward direction, the energy of the blood flow forced the ball or disc to the back of the cage allowing blood to flow through the valve. When blood attempted to flow in a reverse direction, or "regurgitate", the energy of the blood flow forced the ball or disc into the orifice in the valve and blocked the flow of blood.

A bi-leaflet valve comprised an annular valve body in which two opposed leaflet occluders were pivotally mounted. The occluders were substantially rigid and moved between a closed position, in which the two leaflets were mated and blocked blood flow in the reverse direction, and an open position, in which the occluders were pivoted away from each other and did not block blood flow in the forward direction. The energy of blood flow caused the occluders to move between their open and closed positions.

A tri-leaflet valve comprised an annular valve body in which three leaflets were mounted to a portion of the valve body, called a "stent," located at the circumference of the annulus. When blood flowed in the forward direction, the energy of the blood flow deflected the three leaflets away from the center of the annulus and allowed blood to flow through. When blood flowed in the reverse direction, the three leaflets engaged each other in a coaptive region, occluded the valve body annulus and prevented the flow of blood. The valve leaflets were made from tissue, such as specially treated porcine or bovine pericardial tissue, or from man-made materials such as ceramic materials, elastomers or other biocompatible polymers.

It is important in heart valve design to reduce the forward (systolic) pressure necessary to open the heart valve.

SUMMARY OF THE INVENTION

In general, in one aspect, the invention features a heart valve comprising a valve body having an axis. A plurality of flexible leaflets is coupled to the valve body. Each of the plurality of leaflets has an open position and a closed position. Each of the plurality of leaflets has a bottom and each of the plurality of leaflets has a center of a free margin. One or more of the plurality of leaflets comprises a spine. The spine has a different curvature than the non-spine portion of the leaflet. The spine comprises a longitudinal axis. The inclination of the axis of the spine with respect to a line from the bottom of the leaflet to the center of the free margin is less than 10 degrees.

Implementations of the invention may include one or more of the following. The axis of the spine may be parallel to the line from the bottom of the leaflet to the center of the free margin.

In general, in another aspect, the invention features a heart valve comprising a valve body having an axis. A plurality of flexible leaflets is coupled to the valve body. Each of the plurality of leaflets has an open position and a closed position. One or more of the plurality of leaflets comprises a longitudinal spine. The spine has an axis and the inclination of the spine axis with respect to the valve body axis is greater than 0 degrees.

Implementations of the invention may include one or more of the following. The inclination of the spine axis with respect to the valve body axis may be greater than 5 degrees.

In general, in another aspect, the invention features a heart valve comprising a valve body having an axis. The valve body has an orifice, the orifice having an inside diameter. The heart valve comprises a plurality of flexible leaflets. One or more of the plurality of leaflets comprises a spine. The one or more leaflets with a spine further comprise a transition point between the spine and the non-spine portion of the leaflet. The transition point is located at a distance from the axis. The distance is at least twenty percent of the distance from the axis to the inside of the valve body.

In general, in another aspect, the invention features a heart valve comprising a valve body and a plurality of flexible leaflets coupled to the valve body. The plurality of leaflets has an open position and a closed position. Each of the plurality of leaflets comprises a belly when the plurality of leaflets are in their respective closed positions. The belly of one or more of the plurality of leaflets has a continuous curvature except for a non-continuous portion.

Implementations of the invention may include one or more of the following. The non-continuous portion of the belly may be generally cylindrical. The non-continuous portion of the belly may be generally planar. The continuous portion of the belly may have a generally cylindrical shape having a first axis and the non-continuous portion of the belly may have a generally cylindrical shape having a second axis. The first axis may intersect the second axis above the intersection of the leaflet and the valve body. The non-continuous portion may have a longitudinal axis and a cross-section of the non-continuous portion generally perpendicular to the axis of the spine may be generally V-shaped. The belly of the one or more of the plurality of leaflets may be symmetrical about an axis. The non-continuous portion may have a longitudinal axis. The belly axis may not coincide with the axis of the non-continuous portion. Each of the one or more of the plurality of leaflets may have a center of a free margin and a bottom point. The non-continuous portion may have a longitudinal axis extending along a line from the bottom point of the leaflet to the center of the free margin of the leaflet.

In general, in another aspect, the invention features a heart valve comprising a valve body and a plurality of flexible leaflets coupled to the valve body. Each leaflet has a thickness. Each of the one or more of the plurality of leaflets comprises a buckle-susceptible portion, the thickness of the buckle-susceptible portion being different from the thickness of the remaining portion of the leaflet.

Implementations of the invention may include one or more of the following. The thickness of the buckle-susceptible portion may be less than the thickness of the remaining portion of the leaflet. The thickness of the buckle-susceptible portion may not be uniform.

In general, in another aspect, the invention features a method for opening a closed heart valve comprising a plurality of flexible leaflets, comprising experiencing pressure from an inflow direction of the valve. The method further comprises collapsing a spine portion of a leaflet before the remaining portion of the leaflet collapses.

Implementations of the invention may include one or more of the following. The leaflet has a thickness and the spine portion may comprise a region where the leaflet has a decreased thickness. Each of the plurality of leaflets may have an open position and a closed position. Each of the plurality of leaflets may have a center of a free margin when it is in its respective closed position. The method may comprise pulling the center of the free margin of the leaflet with the spine away from the centers of the free margins of the other leaflets before the remaining portion of the leaflet pulls away from the other leaflets by the spine portion of the leaflet collapsing and pulling the center of the free margin. Collapsing may comprise retaining generally the curvature of the spine portion of the leaflet. Collapsing may comprise changing the curvature of the spine portion of the leaflet from a flat curvature to a curvature that is convex, deflected in the direction of the pressure. Collapsing may comprise changing the curvature of the spine portion of the leaflet from a V-shaped curvature to a rounded V-shape, deflected in the direction of the pressure. Collapsing may comprise changing the curvature of a subset of the spine portion of the leaflet from a deflection in a first direction to a deflection in a second direction and retaining generally the curvature of the remainder of the spine portion of the leaflet.

In general, in another aspect, the invention features a heart valve comprising a valve body. A plurality of flexible leaflets are coupled to the valve body. Each leaflet has an open position and a closed position. Each leaflet comprises a belly having a predominately first curvature in the open position and a predominately second curvature in the closed position. One or more of the plurality of leaflets comprises an expansion feature. The expansion feature is configured so that the belly of the leaflet has more surface area of the first curvature in the open position than it has of the second curvature in the closed position.

Implementations of the invention may include one or more of the following. The expansion feature may comprise a fold. The expansion feature may have the first curvature in the open position.

DESCRIPTION OF THE PREFERRED EMBODIMENTS

Figure 1:
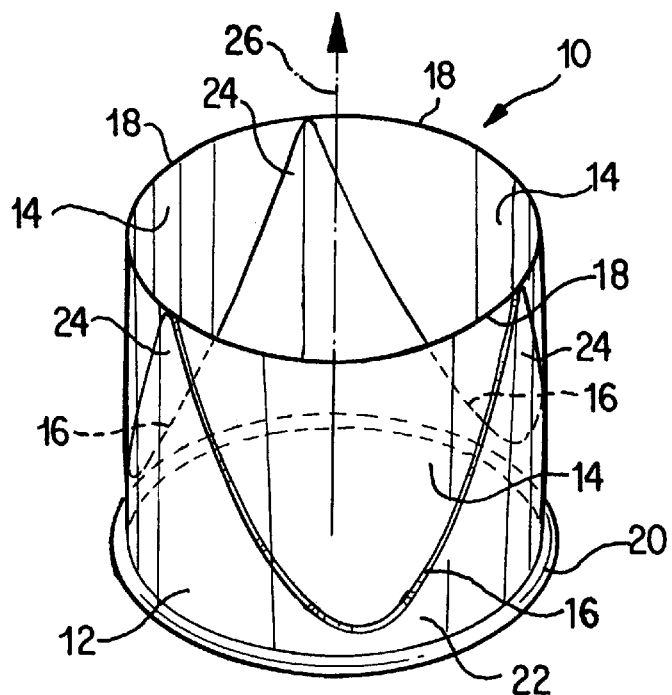
FIG. 1 is a perspective view of a polymer valve.

A tri-leaflet heart valve prosthesis 10 comprises an annular elastic valve body 12 and three flexible leaflets 14 made of a biocompatible polymer such as silicone or polyurethane, as shown in FIG. 1. Each leaflet has an attachment edge by which it is coupled to the valve body along an attachment curve 16. Each leaflet has a free edge 18 that is not coupled to the valve body. A sewing ring 20 is coupled to the base of the valve body 12 and provides a place for sutures to be applied when the valve is implanted. The valve body comprises an annular base 22 and a leaflet support, comprising three shaped posts 24, that supports the leaflets 14.

Figure 2:
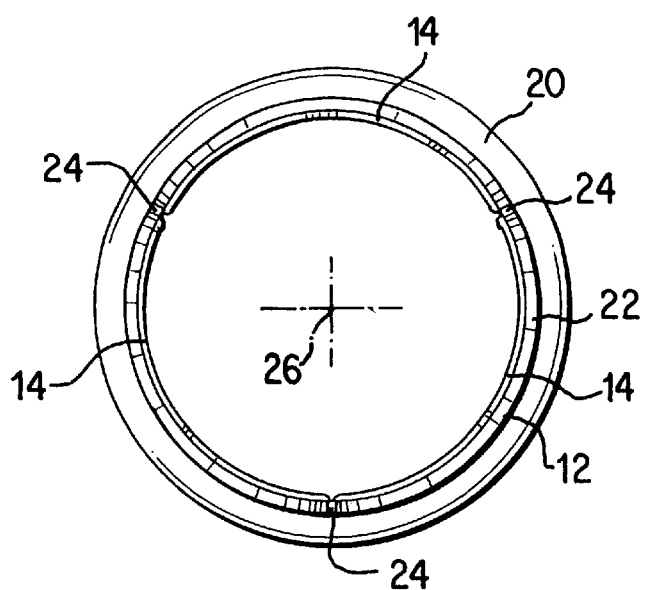
FIG. 2 is a top view of the polymer valve of FIG. 1.

When fluid flow is in the forward direction, i.e. in the direction of the arrow shown in FIG. 1, the pressure of the blood flow causes the leaflets 14 to deflect away from a central longitudinal axis 26 of the valve body that is generally parallel to the three posts 24. In this "open" position, the leaflets 14 define a large flow orifice, having an inside surface 23 defining an inside diameter as shown in FIG. 2. With the leaflets in the open position shown in FIGS. 1 and 2, the valve presents little resistance to fluid flow.

Figure 3:
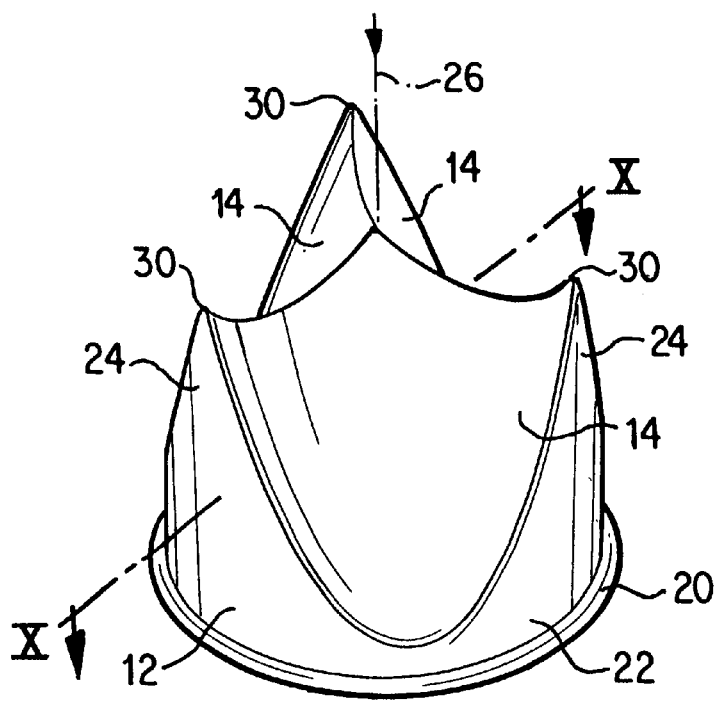
FIG. 3 is a perspective view of a polymer valve.
Figure 4:
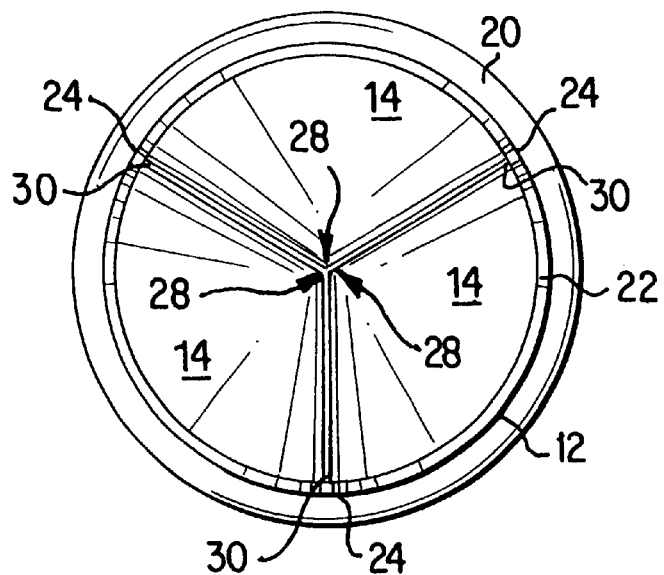
FIG. 4 is a top view of the polymer valve of FIG. 3.

When the pressure of blood flow is insufficient to overcome the elastic force biasing the valve toward a closed or partially closed position, the leaflets deflect toward axis 26, as shown in FIGS. 3 and 4. In this "closed" position, each leaflet would occlude more than one-third of the valve body's orifice were it not for the presence of the other leaflets. Consequently, when the three leaflets deflect toward axis 26, they engage each other and form coaptive areas along the free edges 18, which help the valve seal against reverse flow. Further, when the leaflets press together, each leaflet forms a "triple point" 28 at the point where the three leaflets come together, as shown in FIG. 4. The place where the leaflets 14 come together adjacent the posts 24 is called the "commissure" 30, as shown in FIG. 3.

In most prior art heart valves, the flexible leaflets in their closed positions are generally planar in their coaptive regions and have a generally spherical shape in the region below the coaptive region, called the "belly". The pressure of blood flowing in a forward direction impinges on the convex side of the leaflets urging them from the closed positions shown in FIGS. 3 and 4 to the open positions shown in FIGS. 1 and 2. To make that transition, the blood pressure must overcome the resistance of the leaflets to buckling.

Figure 5A:
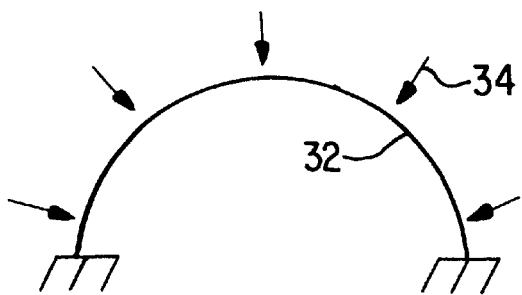
FIGS. 5a–d are cross-sectional views of a prior art leaflet being subjected to forward pressure.

This is illustrated in FIGS. 5a–d. A leaflet 32, the belly of which has a cylindrical cross-section as shown in FIG. 5a, has pressure 34, representing the pressure of blood attempting to flow in the forward direction (the direction of the arrow in FIG. 1) impinging on its convex side. The leaflet 32 resists displacement.

Figure 5B:
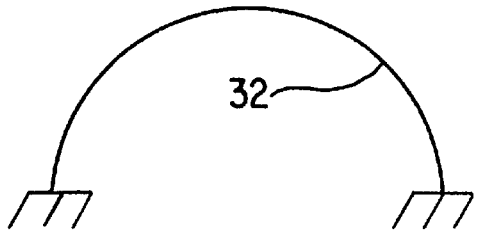
Figure 5C:
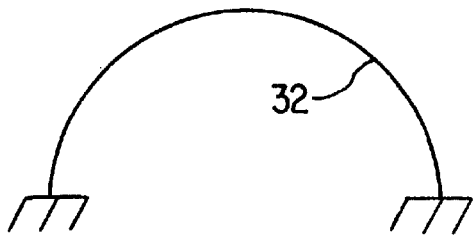

As the pressure 34 increases, indicated by FIGS. 5b and 5c, the leaflet continues to resist displacement from its original position. Finally, when the pressure reaches a particular level the leaflet buckles and transitions from its closed position to its open position, illustrated in FIG. 5d.

A "feature" is introduced into the shape of the leaflet 32, which causes the leaflet to transition from its closed position to its open position at a lower forward pressure. The feature can be any change in the leaflet that reduces its resistance to buckling including a change in the curvature of the leaflet that causes the resulting leaflet to have a non-continuous shape or a reduction in the thickness of a portion of the leaflet.

Figure 6A:
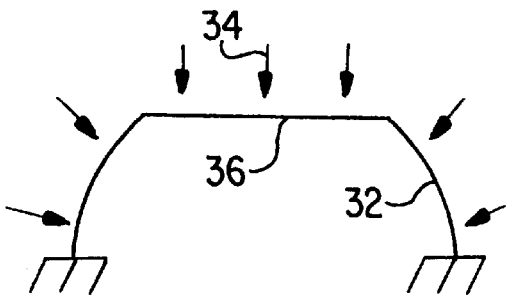
FIGS. 6a–d are cross-sectional views of a leaflet according to the present invention being subjected to forward pressure.
Figure 6B:
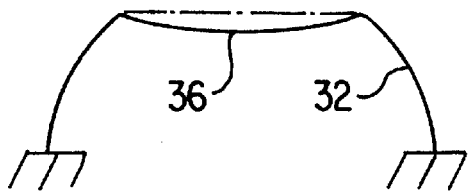
Figure 6C:
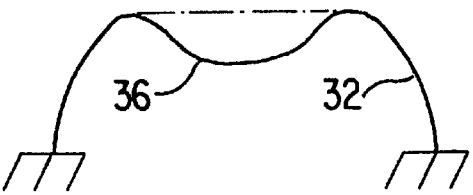
Figure 5D:
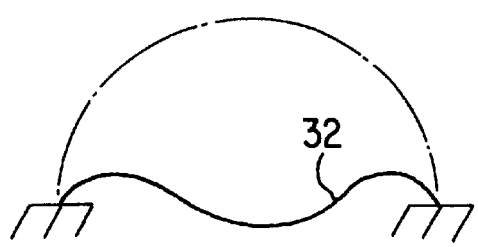
Figure 6D:
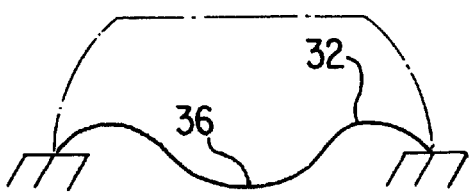

To illustrate a change in the curvature of the leaflet, a planar portion 36 can be introduced into the belly of the leaflet 32 so that the belly of the leaflet 32 no longer has a continuous cylindrical shape, as shown in FIG. 6a. As a consequence, the leaflet has a lower resistance to buckling as shown in FIGS. 6b–d. In FIG. 6b, in which the leaflet 32 is experiencing the same forward pressure as in FIG. 5b, the planar portion 36 has begun to deflect in the direction of the forward pressure. In FIG. 6c, in which the leaflet 32 is experiencing the same forward pressure as in FIG. 5c, the buckling of the planar portion 36 has begun to cause the remainder of the leaflet to buckle. Under that same pressure, the leaflet will buckle entirely as shown in FIG. 6d and will make the transition from its closed position to its open position.

Figure 7A:
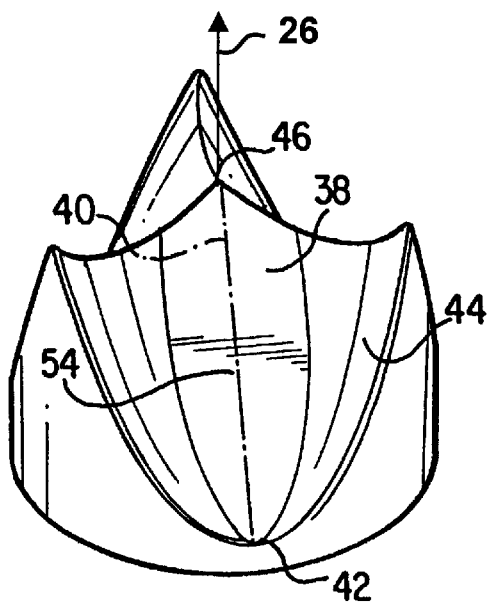
FIGS. 7a–d and 8a–c are perspective views of valves according to the present invention.
Figure 7B:
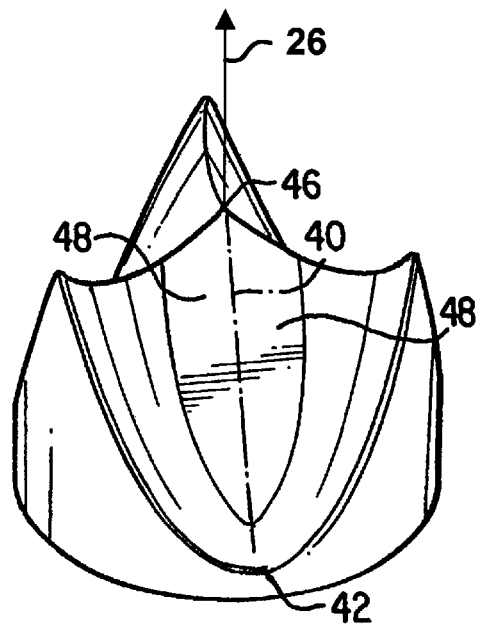
Figure 7C:
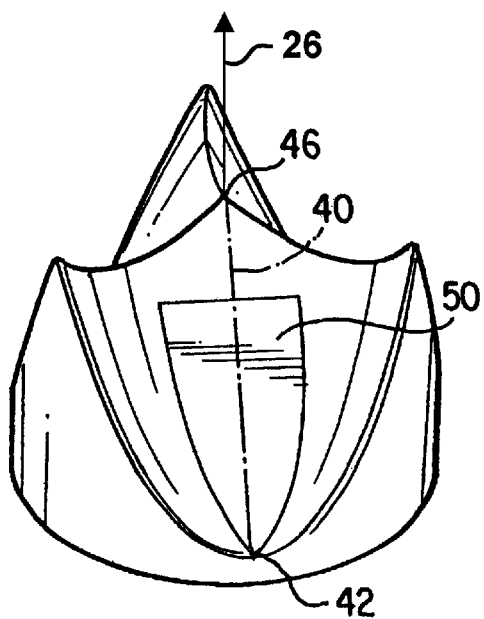
Figure 7D:
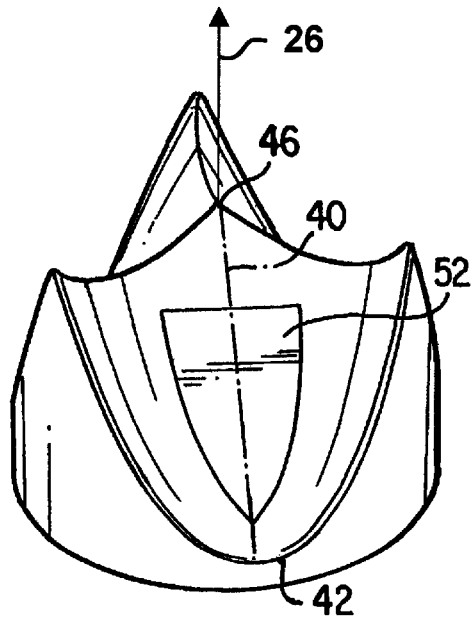

In one embodiment, illustrated in FIG. 7a, a planar portion 38 extends along a line 40 from the bottom point 42 of the leaflet 44 to the center of the free margin 46 and to a transition point 43 of the leaflet 44. In FIG. 7a, the planar portion extends the entire distance from the bottom point 42 to the center of the free margin 46. In another embodiment, the planar portion 48 extends to the center of the free margin 46 but not to the bottom point 42, as shown in FIG. 7b. The transition point is at least twenty percent of the distance from the axis 26 to the inside surface 23 of the valve body 26. In still another embodiment, the planar portion 50 extends to the bottom point 42 but not to the center of the free margin 46, as shown in FIG. 7c. In still another embodiment, the planar portion 52 extends along the line 40 but does not extend to either the center of the free margin 46 or the bottom point 42.

An axis 54 of the planar portion may be parallel to the line 40 or it may be inclined, preferably by less than ten degrees, with respect to the line. The axis 54 of the planar portion is inclined with respect to the axis of the valve body 26, preferably by at least five degrees.

Figure 8A:
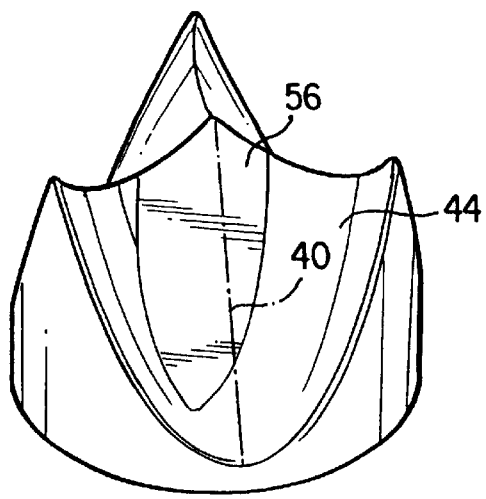
Figure 8B:
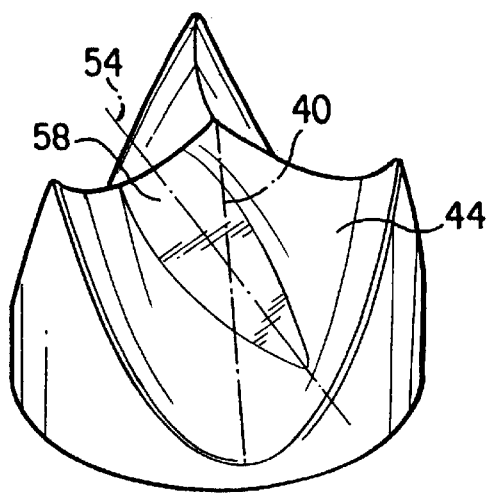
Figure 8C:
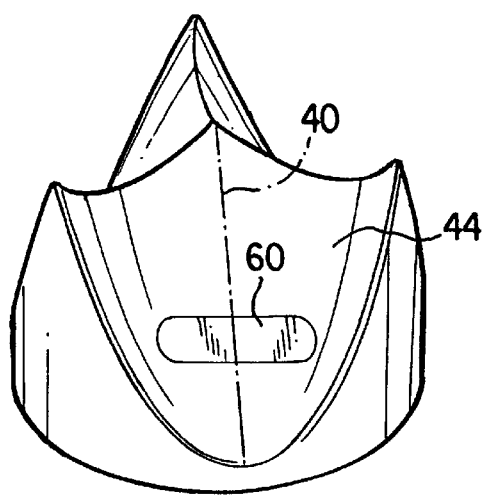

In the embodiments illustrated in FIGS. 7a–d, the planar portion is symmetrical around the line 40 extending from the center of the free margin 46 of the leaflet 44 to the bottom point 42 of the leaflet 44. Such symmetrically located features are called "spines." The planar portion will reduce the leaflet's resistance to buckling even if it is not symmetrically located. Thus, the planar portion 56 may be asymmetrically located with respect to the line 40, as shown in FIG. 8a. Alternatively, the planar portion 58 may be obliquely located with respect to the line, as shown in FIG. 8b. In still another alternative, the planar portion 60 may be transverse to the line 40, as shown in FIG. 8c. In each of these embodiments, the feature may extend to the free margin or attachment curve of the leaflet, as shown in FIGS. 8a and 8b, or the boundaries of the feature may not intersect the boundaries of the leaflet, as shown in FIG. 8c.

Figure 9:
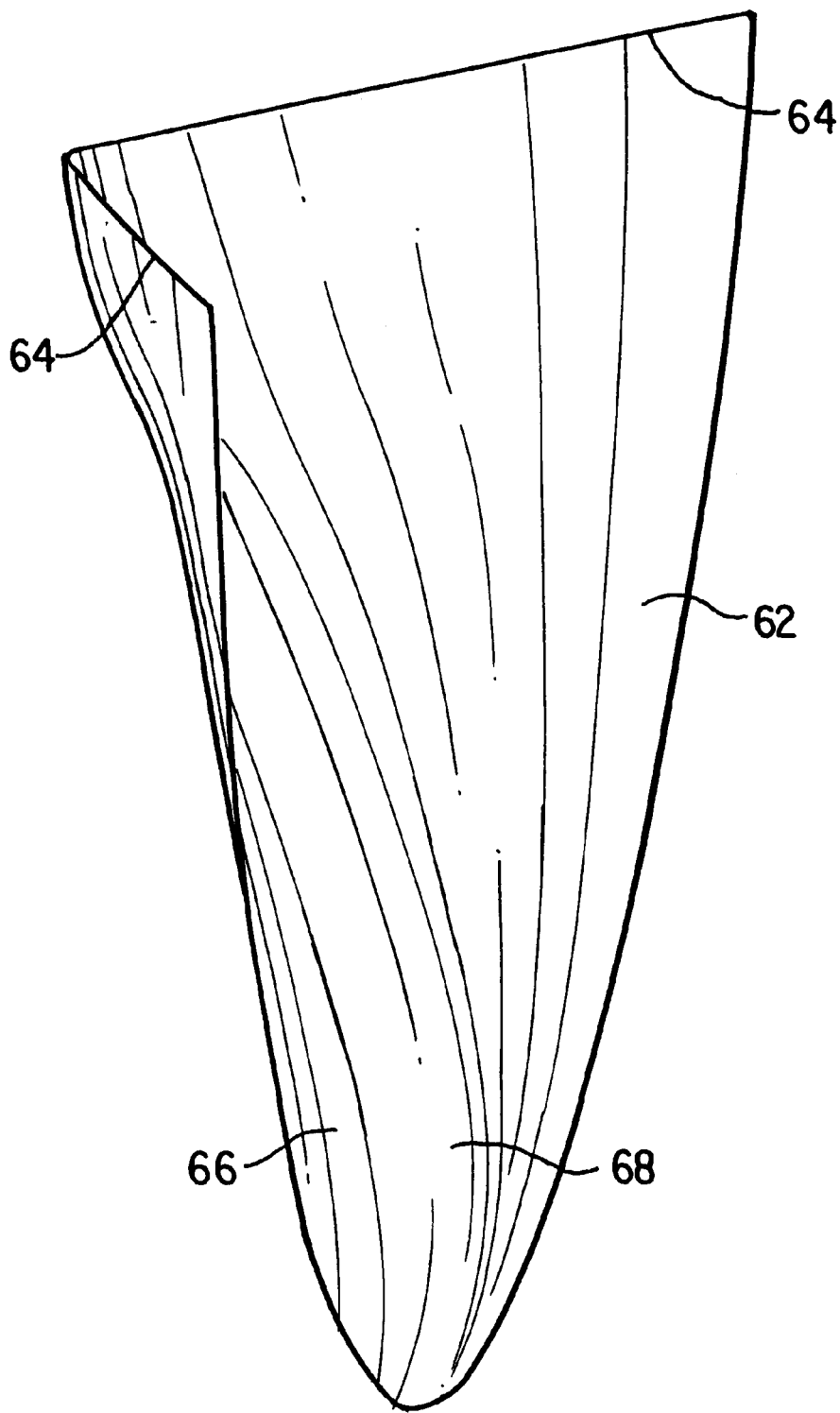
FIG. 9 is a perspective view of a leaflet according to the present invention.

FIG. 9 shows a three dimensional representation of a leaflet 62 in its closed position. The leaflet comprises a region adjacent the free margin 64 and a belly 66. In prior art leaflets, the belly 66 is concave when viewed from the direction shown in FIG. 9. In the embodiment shown in FIG. 9, the belly includes a convex portion 68 that changes the curvature of the belly 66 and makes the leaflet less resistant to buckling and therefore easier to transition from its closed position to its open position. Further, because the leaflet is biased toward opening, it will start opening before the pressure on its inflow side exceeds the pressure on the outflow side. The design of the leaflet shown in FIG. 9 will also have low bending stress when the valve is open.

Figure 10:
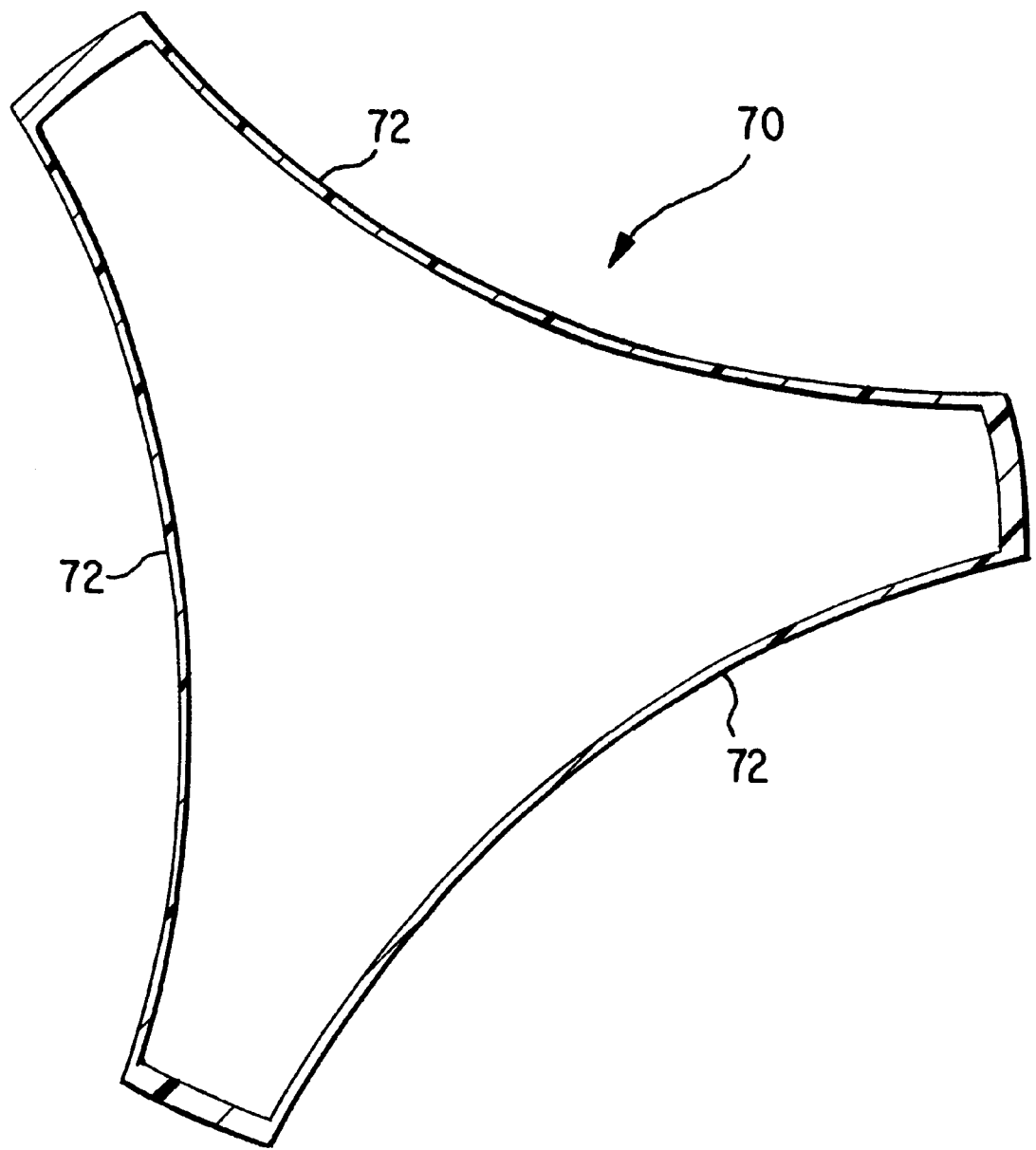
FIG. 10 is a cross-sectional view of a prior art leaflet viewed along lines X in FIG. 3.

FIG. 10 shows a cross-section of a prior art tri-leaflet heart valve 70 in which the leaflets 72 have continuous curvature. The cross-section cuts across the belly portion of the leaflets where the leaflets have a continuous curvature. Features can be introduced into the shape of the leaflets 72 in a variety of ways, all of which will interrupt the continuity of the shape of the leaflet, and in particular the belly portion of the leaflet.

Figure 11:
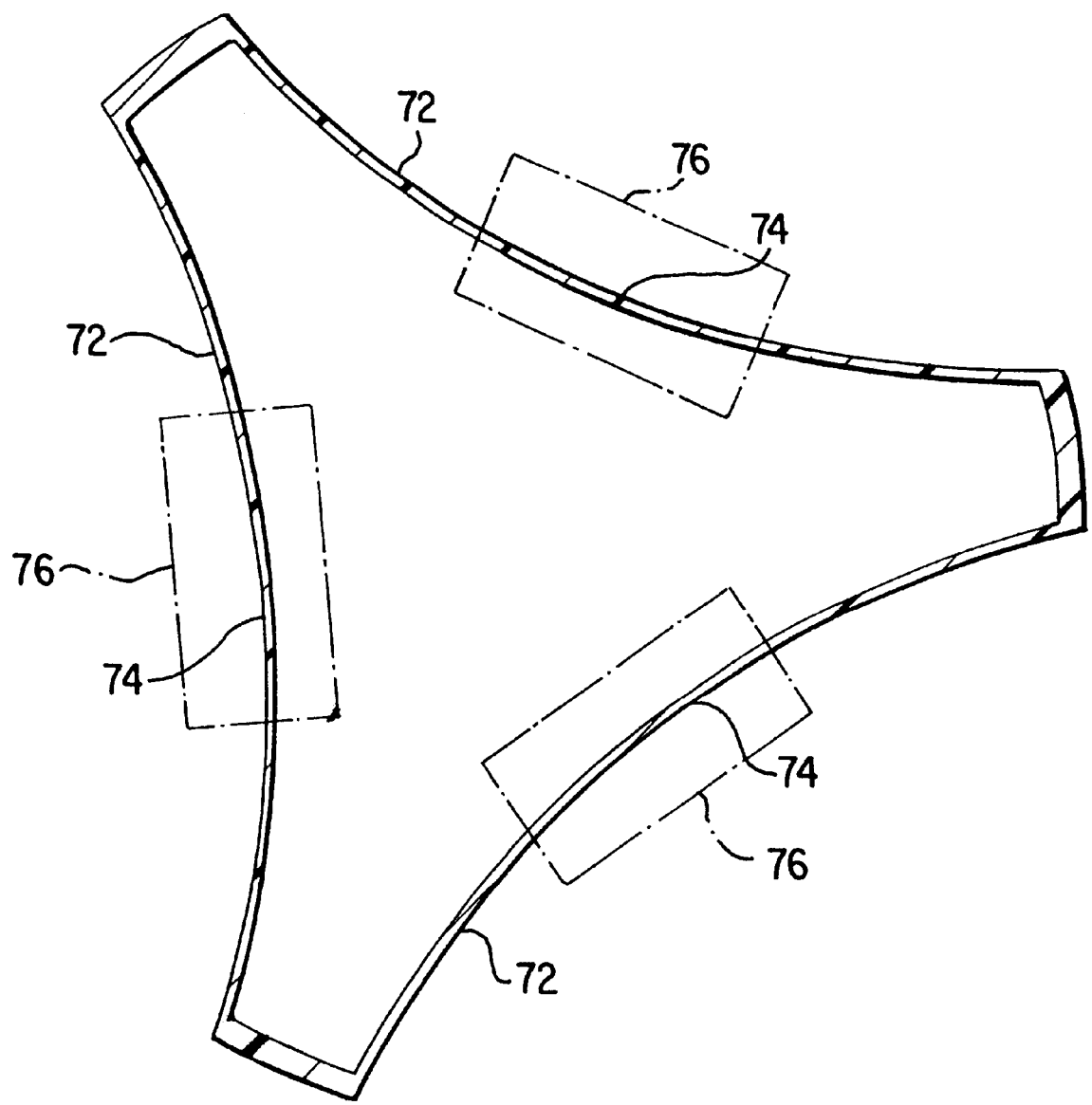
FIGS. 11, 12, 13, 14, 15, 17, 18, 19, 20 and 21 are cross-sectional views of a leaflet according to the present invention viewed along lines X in FIG. 3.

For example, in FIG. 11 the portions 74 of the leaflets 72 enclosed in dashed boxes 76 have been flattened slightly to cause a change in curvature as compared to the portions of the leaflets 72 outside the dashed boxes. This change in curvature is sufficient to reduce the resistance of the leaflets to buckling.

Figure 12:
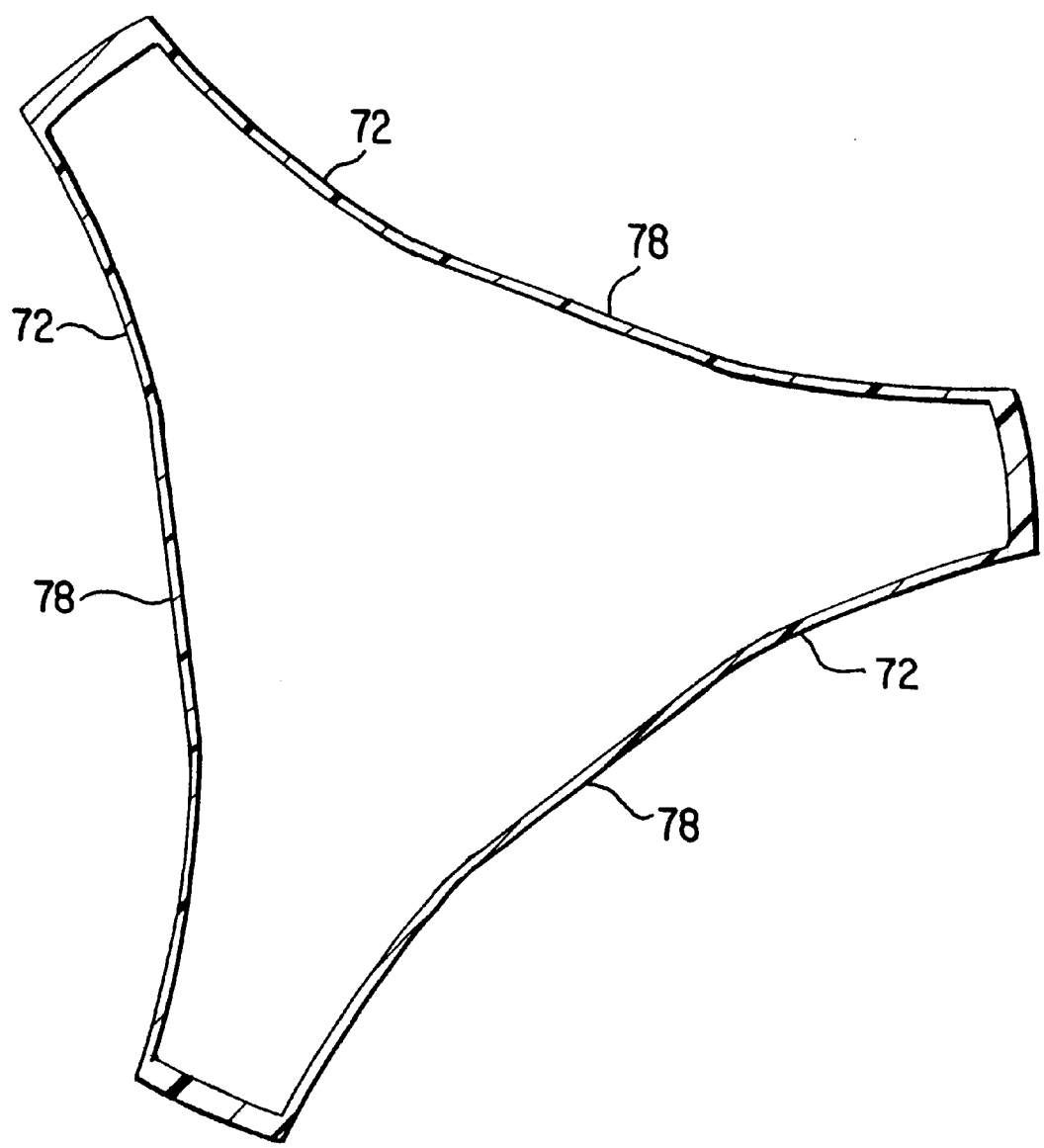
Figure 13:
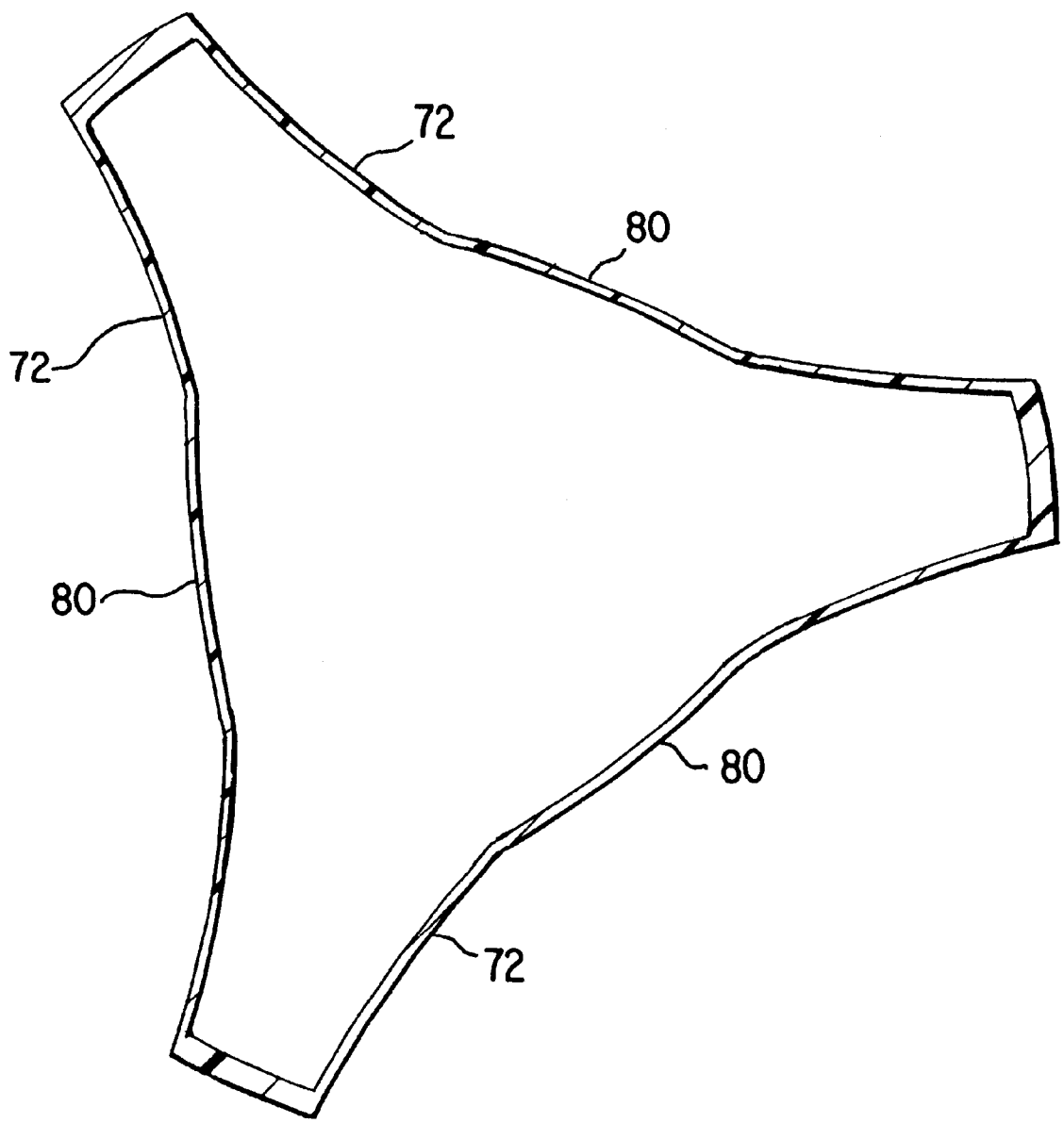
Figure 14:
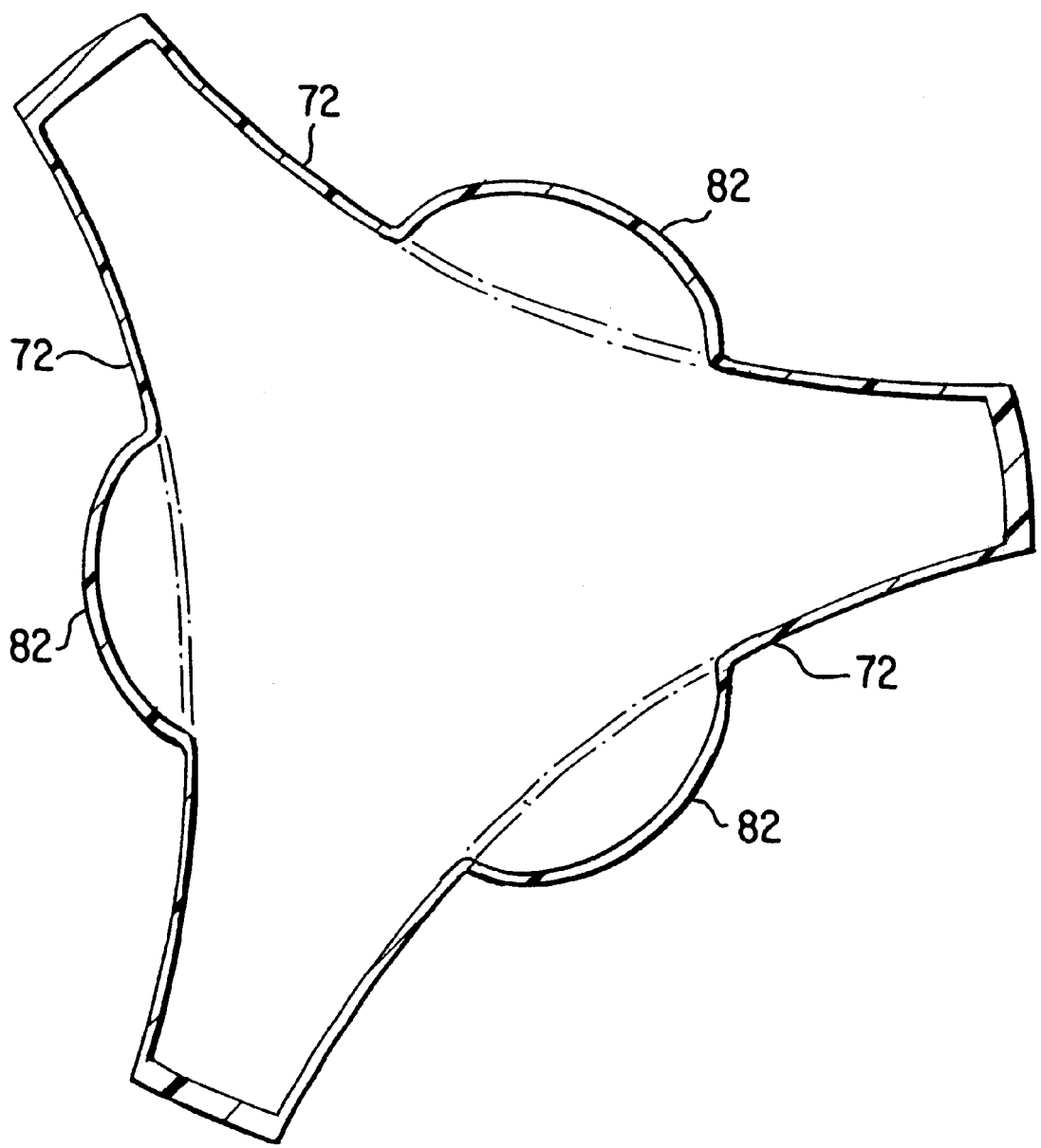
Figure 15:
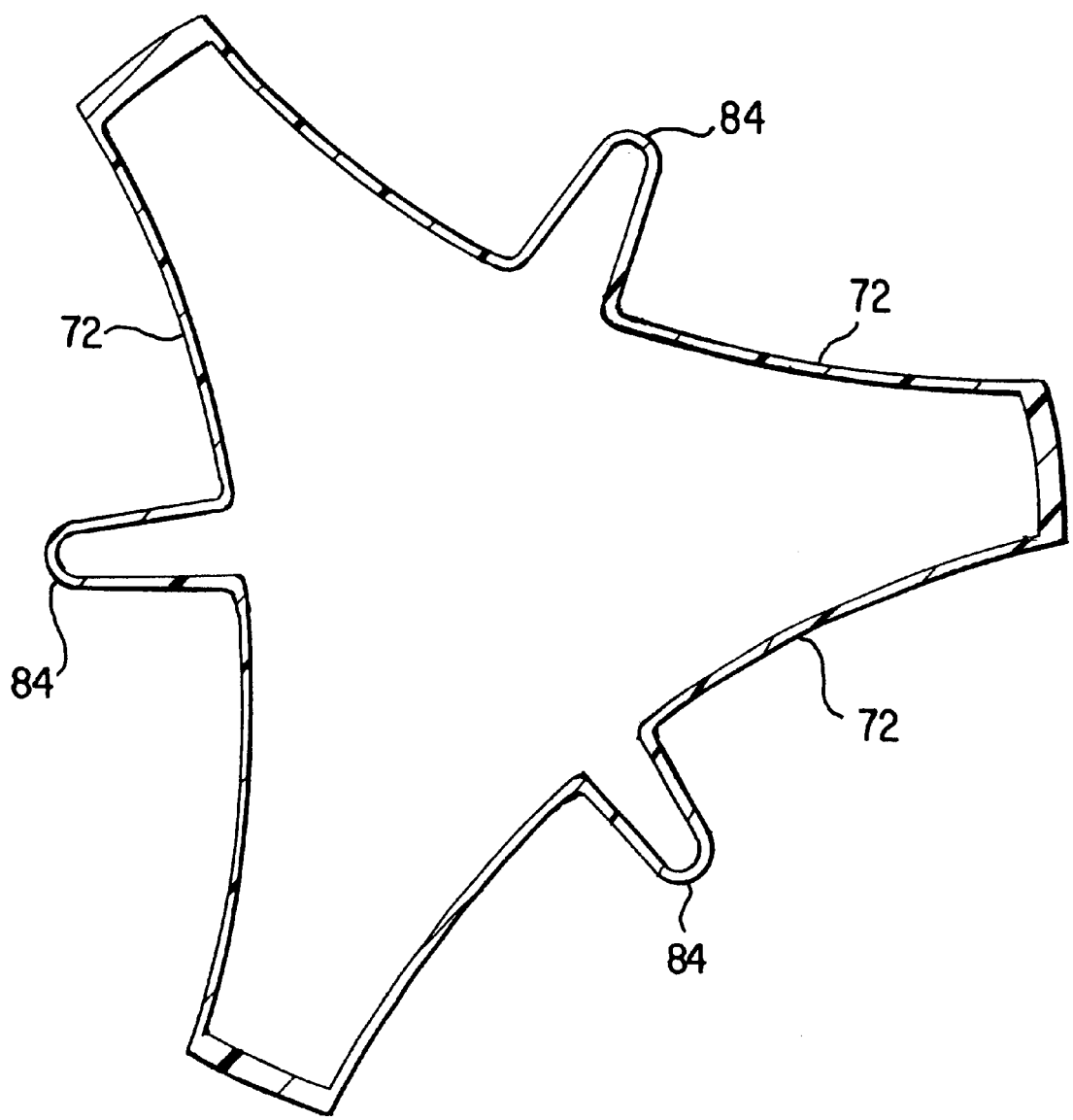
Figure 16:
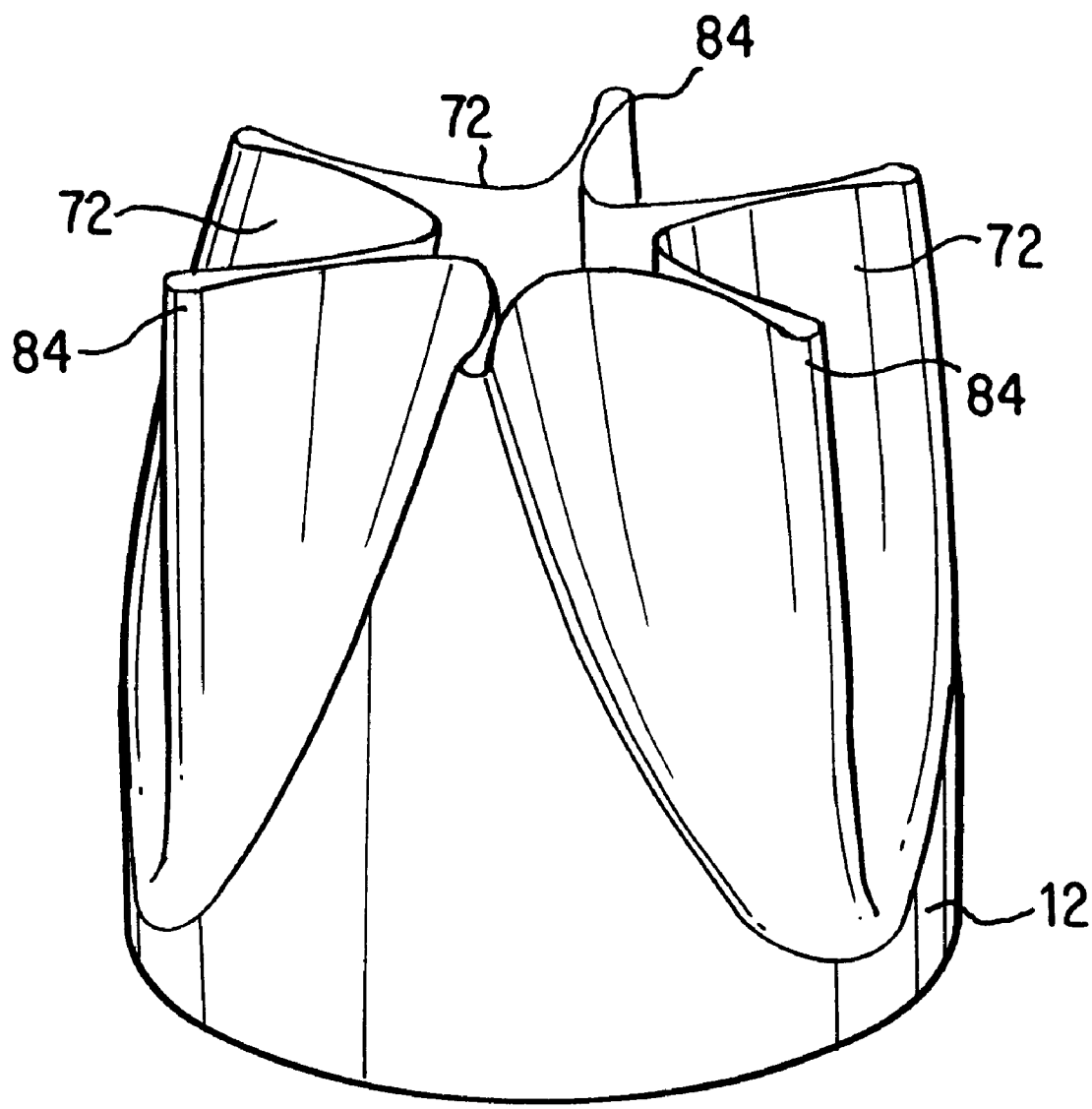
FIG. 16 is a perspective view of a heart valve according to the present invention.
Figure 17:
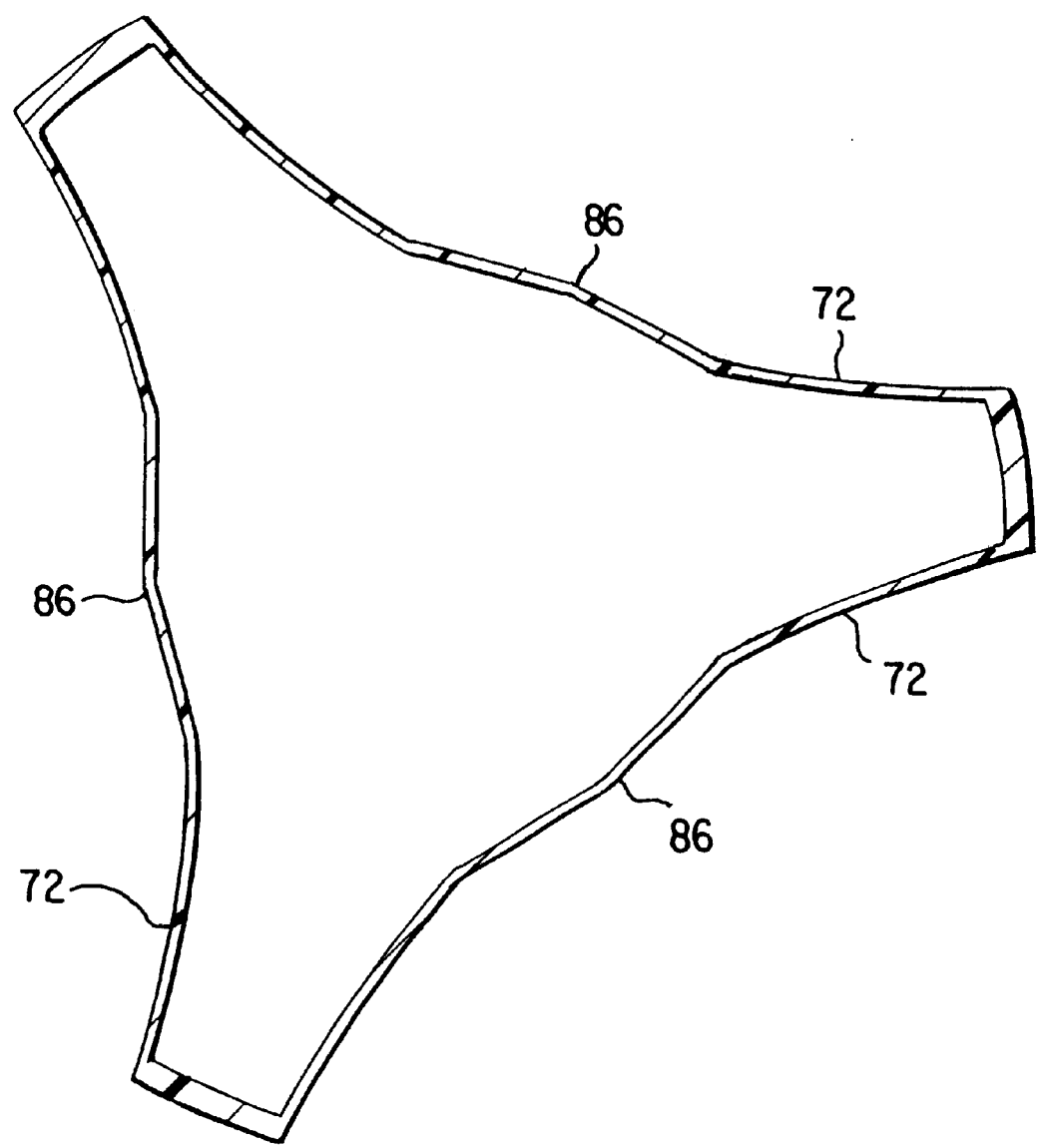

In another embodiment, illustrated in FIG. 12, planar features 78 have been introduced into the leaflets 72. A cross-section of the valves illustrated in FIGS. 7a–d would have the general appearance of FIG. 12. In another embodiment, illustrated in FIG. 13, convex features 80 are introduced into the otherwise-concave shape of leaflets 72. In still other embodiments, illustrated in FIGS. 14, 15 and 16, semicircular features 82 or folded features 84 are introduced into the leaflets 72. In still another embodiment, peaked features 86 may be introduced into the shape of the leaflets 72, as illustrated in FIG. 17.

Figure 18:
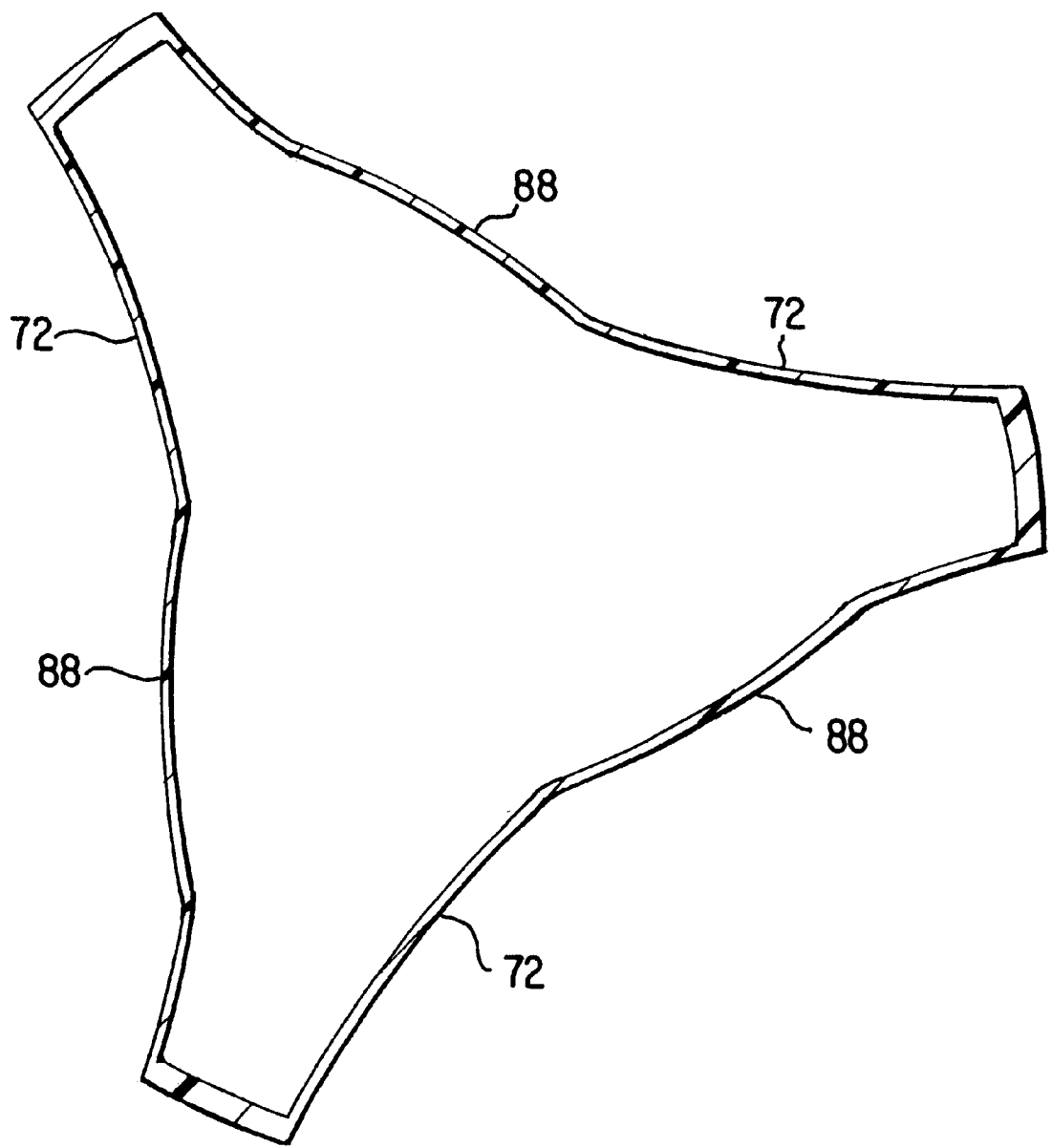

In the embodiments shown in FIGS. 11, 12, 13, 14, 15 and 17, the features are located symmetrically with respect to the leaflets 72. Any of the features illustrated in those figures may be located asymmetrically with respect to the leaflets and still achieve the result of reducing the resistance of the leaflets to buckling. For example, in FIG. 18, concave features 88 are located asymmetrically with respect to the centers of the otherwise-convex leaflets 72.

Figure 19:
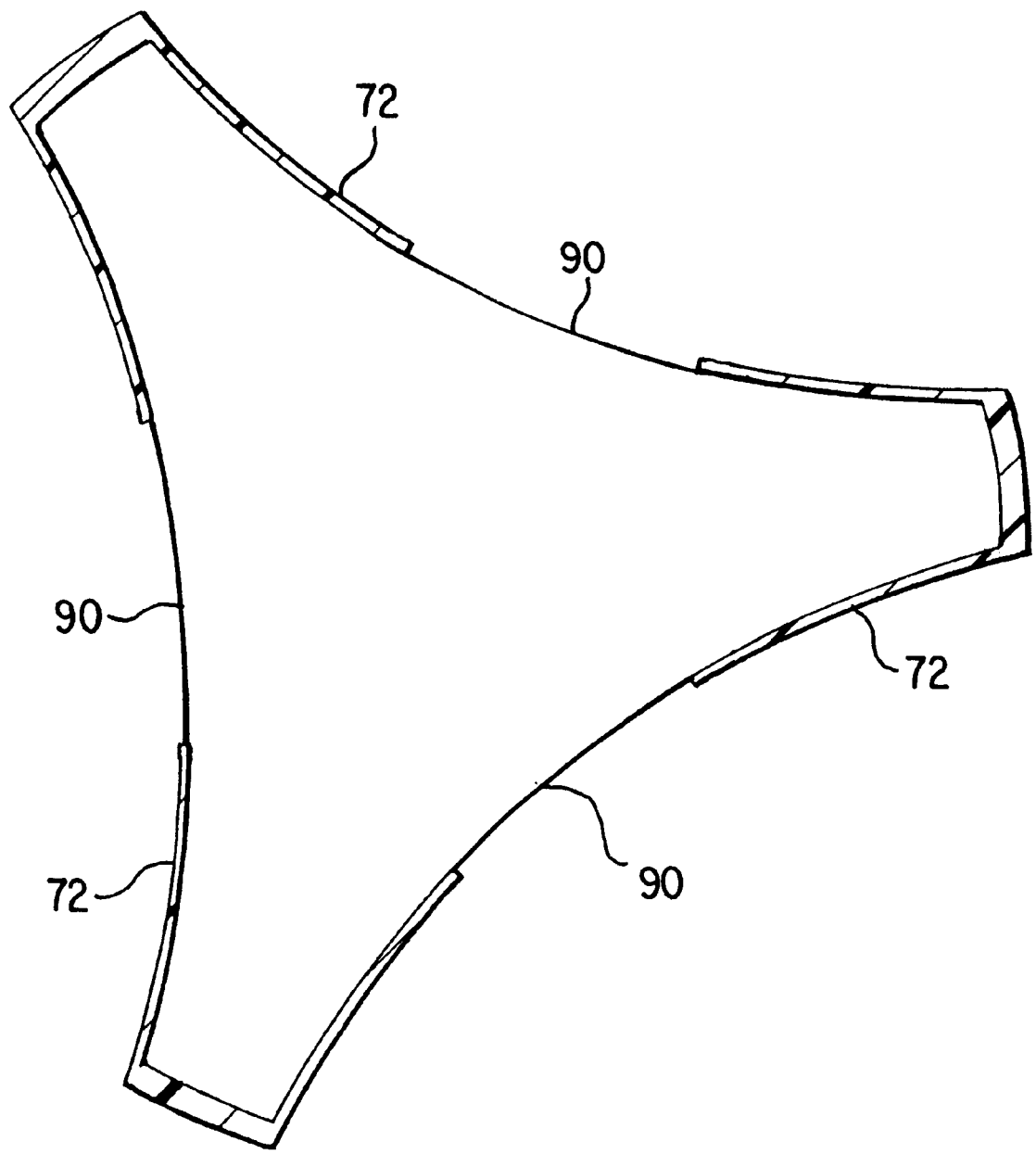
Figure 20:
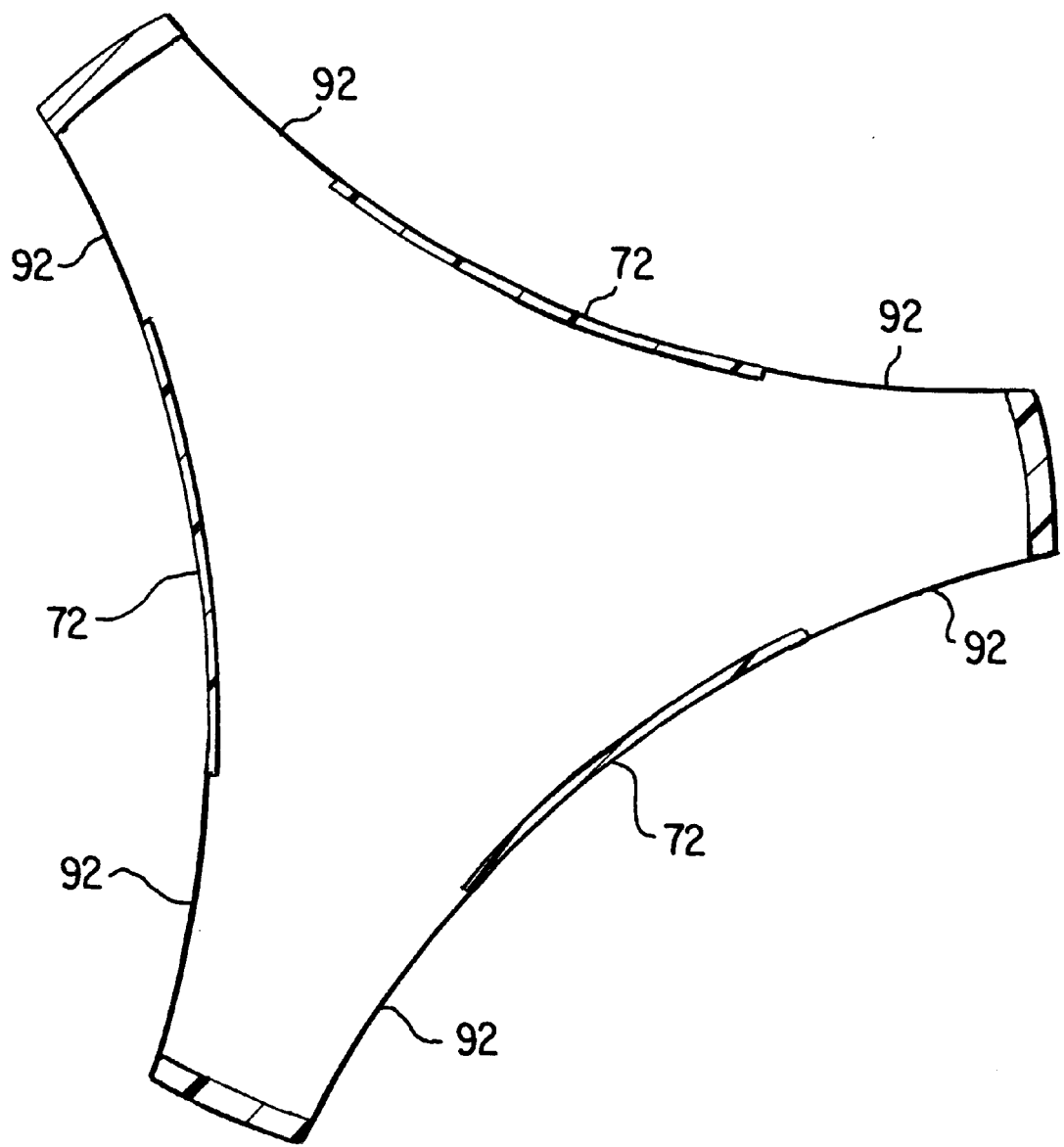

As discussed above, features may also be reductions in the thickness of portions of the leaflet. In FIG. 19 the features are portions 90 of the leaflets 72 where the thickness of the material forming the leaflets is less than in the remaining portion of the leaflets 72. The thinness of the material in the features 90 causes the features 90 to buckle more easily than they would had the material in the portion been the same thickness as in the rest of the leaflet 72. Consequently, each leaflet buckles and transitions from a closed position to an open position more easily. The thin portions 92 of the leaflet can also be located in the "leg" portion of the leaflet 72 along the attachment curve, as shown in FIG. 20.

The thickness of the material forming a feature may vary. For example, the feature may be a spine extending along a line from a leaflet's bottom point to its triple point. The thickness of the material forming the spine may taper from its thickest at the end of the spine closest to the triple point to its thinnest at the end of the spine closest to the bottom point. Alternatively, the material may be thickest at the end of the spine closest to the bottom point. The taper may be gradual and uniform or it may include a step increase or some other non-linear variation in thickness.

Figure 21:
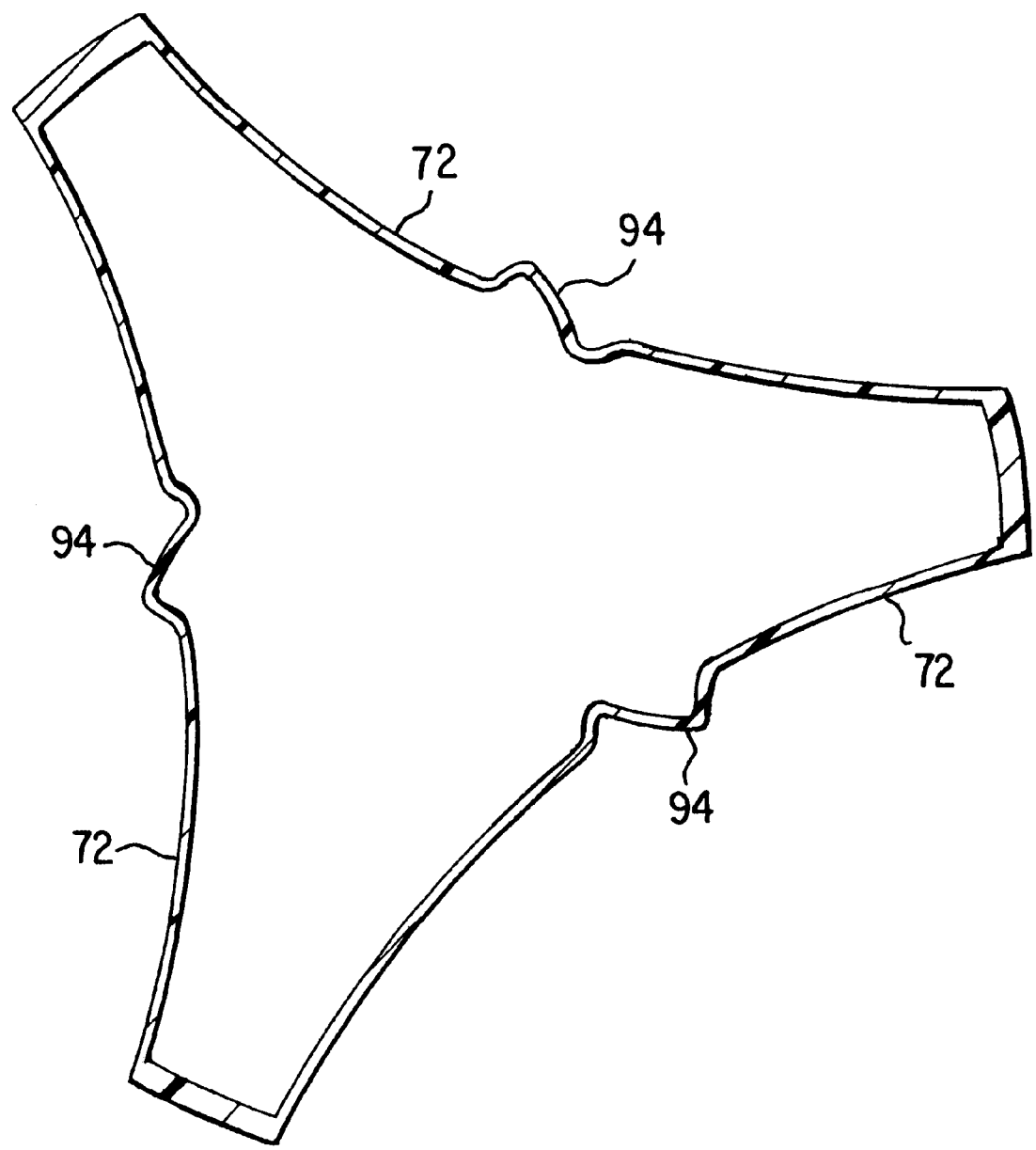

Further, the features can have any arbitrary shape, including the sine-wave shape of the features 94 illustrated in FIG. 21, as long as the continuity of the shape of the leaflets is interrupted by the feature or features.

Figure 22:
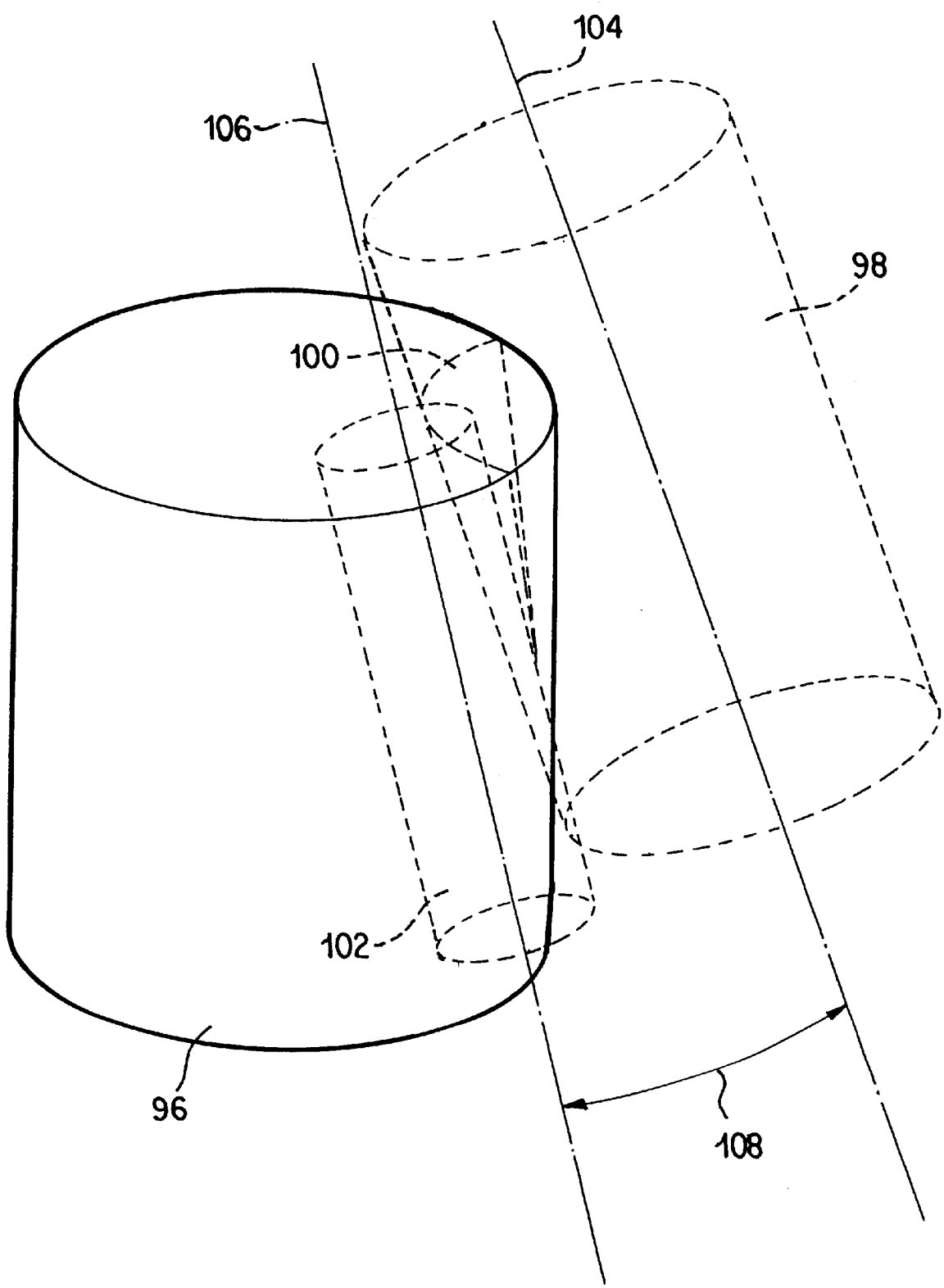
FIG. 22 is a perspective view of the geometry of a leaflet according to the present invention.

For ease of manufacture, the shape of the valve's leaflets is preferably determined by the intersection of solid cylinders, as illustrate in FIG. 22. A cylinder 96 represents the shape of the valve body. The intersection of the valve body cylinder 96 with a second cylinder 98 creates the shape of a cylindrical leaflet 100. A cylindrical feature is added to the shape by intersecting a third cylinder 102 with the intersection of the first two. The second cylinder 98 and the third cylinder 102 each have longitudinal axes 104 and 106, respectively. Preferably, the point of closest approach of the two axes 104 and 106 is above the intersection of the leaflet and the valve body (where the triple point is considered to be above the bottom point). Preferably, the two axes 104 and 106 intersect above the intersection of the leaflet and the valve body. Preferably, the two axes 104 and 106 are not parallel. Even more preferably, the angle 108 between the two axes is greater than one degree. Even more preferably, the angle 108 between the two axes is about three degrees.

Some of the embodiments illustrated above, particularly the embodiment shown in FIGS. 15 and 16, have the advantage of providing additional surface area for the leaflet 72. Consequently, when the leaflet is in the open position, leaflets 72 open wider and the orifice illustrated in FIGS. 1 and 2 is larger, which decreases the valve's resistance to the flow of blood, a desirable characteristic in a heart valve. Further, in these embodiments, the membrane stresses in the leaflet are reduced because the leaflet does not need to be forced into a fully open position to form the orifice illustrated in FIGS. 1 and 2.

The apparatus is not limited to one feature per leaflet. Instead, more than one feature (e.g. a planar portion and a sine wave portion or weakened legs and a planar portion) can be incorporated into a single leaflet. Further, each leaflet may have a different combination of features or one or more of the leaflets on a valve may be entirely free of features. Each feature may incorporate a variety of mechanisms to increase the leaflet's susceptibility to buckling, including incorporating one or more of the feature shapes within a single feature and varying the material thickness within the feature. Moreover, the features described above may be added to valves other than tri-leaflet heart valves, including single leaflet heart valves, bi-leaflet heart valves or valves having more than three leaflets.

The foregoing describes preferred embodiments of the invention and is given by way of example only. The invention is not limited to any of the specific features described herein, but includes all variations thereof within the scope of the appended claims.

What is claimed is:

1. A heart valve comprising
   a valve body having an axis;
   a plurality of flexible leaflets coupled to the valve body, each of the leaflets having
   1) an open position;
   2) a closed position;
   3) an attachment edge coupling said leaflet to the valve body said attachment edge having a bottom point; and
   4) a free edge not coupled to the valve body said free edge being above said attachment edge and having a center point;
   5) a line between said center point and said bottom point, and
   6) a curved belly portion not contacting any other leaflet;
   at least one of the plurality of leaflets comprising a spine area in said belly, the spine area being generally symmetrical around said line and having a different curvature than the non-spine portion of the belly.

2. The heart valve of claim 1 wherein the spine area extends from said center point to said bottom point.

3. The heart valve of claim 1, wherein the valve body further comprises a flow orifice having an inside surface and a diameter, and wherein said leaflet further comprises a transition point between the spine portion and the non-spine portion of the belly, the transition point being located at a distance from the axis that is at least twenty percent of the distance from the axis to the inside surface of the valve body.

4. A method for opening a closed heart valve comprising
   1) providing a heart valve having a plurality of flexible polymeric leaflets, at least one leaflet having a curved belly in a closed position said belly not contacting any other leaflet, and a region in said belly that is more susceptible to buckle than the rest of said belly, and
   2) providing pressure from an inflow direction of the valve, wherein the pressure collapses said region of said at least one leaflet before the remaining portion of the leaflet collapses.

5. The method of claim 4 wherein
   the leaflet has a thickness and the region has a decreased thickness.

6. The method of claim 4 further comprising
   1) providing each of said leaflets with a free margin, said free margin having a center, and wherein said at least one leaflet comprises exactly one leaflet; and
   2) pushing the center of the free margin of the leaflet with the region away from the centers of the free margins of the other leaflets before the remaining portion of the leaflet pulls away from the other leaflets.

7. The method of claim 4 wherein collapsing comprises retaining generally the curvature of the region of the leaflet.

8. The method of claim 4 wherein collapsing comprises changing the curvature of the region of the leaflet from a flat curvature to a curvature that is convex, deflected in the direction of the pressure.

9. The method of claim 4 wherein collapsing comprises changing the curvature of the region of the leaflet from a V-shaped curvature to a rounded V-shape, deflected in the direction of the pressure.

10. The method of claim 4 wherein collapsing comprises changing the curvature of a subset of the region of the leaflet from a deflection in a first direction to a deflection in a second direction; and
    retaining generally the curvature of the remainder of the region of the leaflet.

11. The heart valve of claim 1 wherein the spine area extends from said center point but not to said bottom point.

12. The heart valve of claim 1 wherein the spine area extends from said bottom point but not to said center point.

13. The heart valve of claim 1 wherein the spine area extends along said line but does not extend to either said center point or said bottom point.

14. The heart valve of claim 1 wherein the spine area is generally planar.

15. The heart valve of claim 1 wherein the non-spine portion of the curved belly is generally concave and the spine area is concave but has a flatter curvature than the non-spine portion of the belly.

16. The heart valve of claim 1 wherein the non-spine portion of the curved belly is generally concave and the spine area is generally convex.

17. The heart valve of claim 16 wherein the spine area is circular.

18. The heart valve of claim 16 wherein the spine area comprises a fold.

19. The heart valve of claim 1 wherein the non-spine portion of the curved belly is generally concave and the spine area is peaked.

20. The heart valve of claim 1 wherein the non-spine portion of said belly is generally a portion of a first cylinder and said spine area is generally a portion of a second cylinder.

21. The heart valve of claim 20 wherein said first and second axes intersect.

22. The heart valve of claim 21 wherein the first and second axes intersect at an angle greater than one degree.

23. The heart valve of claim 22 wherein the first and second axes intersect at an angle of about three degrees.

* * * * *